(12) United States Patent
Wu et al.

(10) Patent No.: US 11,485,999 B2
(45) Date of Patent: Nov. 1, 2022

(54) METAGENOMICS FOR MICROBIOMES

(71) Applicant: Trace Genomics, Inc., Burlingame, CA (US)

(72) Inventors: Di Wu, San Francisco, CA (US); Pavel Martinov Konov, San Francisco, CA (US); David Curtis Stone, San Francisco, CA (US)

(73) Assignee: Trace Genomics, Inc., Redwood City, CA (US)

( * ) Notice: Subject to any disclaimer, the term of this patent is extended or adjusted under 35 U.S.C. 154(b) by 980 days.

(21) Appl. No.: 16/232,928

(22) Filed: Dec. 26, 2018

(65) Prior Publication Data

US 2019/0194742 A1     Jun. 27, 2019

Related U.S. Application Data

(60) Provisional application No. 62/610,131, filed on Dec. 22, 2017.

(51) Int. Cl.
| | |
|---|---|
| *C12Q 1/6869* | (2018.01) |
| *G16B 40/00* | (2019.01) |
| *G16B 50/00* | (2019.01) |
| *C12Q 1/686* | (2018.01) |
| *G16B 40/20* | (2019.01) |
| *G16B 20/00* | (2019.01) |
| *C12Q 1/689* | (2018.01) |
| *G16B 30/00* | (2019.01) |

(52) U.S. Cl.
CPC .......... *C12Q 1/6869* (2013.01); *C12Q 1/686* (2013.01); *C12Q 1/689* (2013.01); *G16B 20/00* (2019.02); *G16B 40/00* (2019.02); *G16B 40/20* (2019.02); *G16B 50/00* (2019.02); *G16B 30/00* (2019.02)

(58) Field of Classification Search
None
See application file for complete search history.

(56) References Cited

U.S. PATENT DOCUMENTS

| | | |
|---|---|---|
| 9,315,849 B2 | 4/2016 | Fitzpatrick et al. |
| 2016/0289667 A1 | 10/2016 | Wigley et al. |
| 2016/0371430 A1 | 12/2016 | Mahe et al. |
| 2017/0223947 A1 | 8/2017 | Gall et al. |
| 2017/0261512 A1 | 9/2017 | Anderson |
| 2017/0351811 A1 | 12/2017 | Zhao et al. |

FOREIGN PATENT DOCUMENTS

WO    WO 2017/096385 A1    6/2017

OTHER PUBLICATIONS

Jin, Tao et al. "Taxonomic structure and functional association of foxtail millet root microbiome." GigaScience vol. 6, 10 (2017): 1-12. (Year: 2017).*
European Patent Office, Extended European Search Report, European Patent Application No. 18892187.8, dated Sep. 14, 2021, seven pages.
Mele, P. M. et al. "Application of Self-Organizing Maps for Assessing Soil Biological Quality." Agriculture, Ecosystems and Environment, vol. 126, No. 3-4, Jul. 2008, pp. 139-152.
Thompson, L. R. et al. "A Communal Catalogue Reveals Earth's Multiscale Microbial Diversity." Nature, vol. 551, Nov. 23, 2017, pp. 457-463.
PCT International Search Report and Written Opinion, PCT Application No. PCT/US2018/067445, dated Mar. 14, 2019, 18 pages.
Chang, H.X. et al., "Metagenome-Wide Association Study and Machine Learning Prediction of Bulk Soil Microbiome and Crop Productivity," Frontiers in Microbiology, Apr. 2017, vol. 8, pp. 1-11.
Pasolli, E. et al., "Machine Learning Meta-analysis of Large Metagenomic Datasets: Tools and Biological Insights," PLoS Computational Biology, 2016, vol. 12, No. 7, 18 pages.
Yazdani, M. et al., "Using Machine Learning to Identify Major Shifts in Human Gut Microbiome Protein Family Abundance in Disease," 2016 IEEE International Conference on Big Data, 2016, 9 pages.

* cited by examiner

*Primary Examiner* — G Steven Vanni
(74) *Attorney, Agent, or Firm* — Fenwick & West LLP

(57) ABSTRACT

An analytics system uses metagenomics to generate predictions indicating performance of biological or physical samples. In an embodiment, a method includes determining sequence data of a soil sample. The method further includes determining a plurality of features of the soil sample using the sequence data. The plurality of features is determined based at least in part on a measure of a first microbe detected in the soil sample and a different measure of a second microbe detected in the soil sample. The method further includes inputting the plurality of features to a model trained using measures of the first microbe and the second microbe detected in a plurality of soil samples. The method further includes generating, by the model using the plurality of features, a prediction of physical attribute of a plant grown in the soil sample.

14 Claims, 9 Drawing Sheets

| Pathogen | Crops affected (not exhaustive) |
|---|---|
| Verticillium dahliae | Strawberry, lettuce, celery, potato, walnut, tomato, pepper, melons, cotton, alfalfa |
| Macrophomina phaseolina | Strawberry, pepper, potato, soybean, corn, sorghum, cotton |
| Phytophthora spp. | Strawberry, onions, cucumber, squash, soybean |
| Pythium spp. | Strawberry, soybean, turf |
| Fusarium oxysporum f. sp. lactucae | Lettuce |
| Sclerotinia sclerotiorum | Lettuce, peach, almond, celery, lettuce, soy |
| Colletotrichum | Lettuce, potato, citrus, corn, almond, soy, blueberry, strawberry |
| Botrytis cinerea | Lettuce, grapevine, peach, citrus, cherry, almond, caneberry, blueberry, strawberry |
| Agrobacterium tumefaciens | Nut orchards (walnut, almond), stone fruits |
| Xanthomonas | Nut orchards (walnut, almond, pistachios), corn, lettuce, soy, strawberry |

FIG. 8

METAGENOMICS FOR MICROBIOMES

CROSS REFERENCE TO RELATED APPLICATION

This application claims the benefit of priority to U.S. Provisional Application No. 62/610,131, filed on Dec. 22, 2017, which is incorporated herein by reference in its entirety for all purposes.

TECHNICAL FIELD

This disclosure generally relates to models for metagenomics and predictions associated with biological samples based on microbiomes in the biological samples.

BACKGROUND

The soil microbiome includes thousands of organisms, including bacteria, fungi, nematodes, and insects, among other microbes. Metagenomics (also referred to as environmental genomics or community genomics) may involve developing a profile of the microbiome detected in a biological sample such as soil. As one application, it is desirable to predict whether a farmer's field will produce a high or low crop yield, and also whether the crops will develop disease. Further, it is challenging to determine the impact of particular microbe species (e.g., in soil) on crop yield and disease pressure.

BRIEF DESCRIPTION OF THE FIGURES

The disclosed embodiments have advantages and features which will be more readily apparent from the detailed description, the appended claims, and the accompanying figures (or drawings). A brief introduction of the figures is below.

FIG. 8 illustrates an example pathogen detected by one or more models according to an embodiment.

SUMMARY

An analytics system uses metagenomics to generate predictions, for example, indicating performance of crops grown in certain biological samples. In an embodiment, a method includes determining sequence data of a soil sample. The method further includes determining a plurality of features of the soil sample using the sequence data, which may be indicative of the microbiome of the soil sample. The plurality of features is determined based at least in part on a measure of a first microbe detected in the soil sample and another measure of a second microbe detected in the soil sample. The method further includes inputting the plurality of features to a model trained using measures of the first microbe and the second microbe detected in a plurality of soil samples. The method further includes generating, by the model using the plurality of features, a prediction of physical attribute of a plant grown in the soil sample.

In an embodiment, one or more processors may execute instructions stored by a non-transitory computer-readable storage medium to control a computer system to perform steps of any of the above methods.

DETAILED DESCRIPTION

I. Example System Overview

Figure 1A:
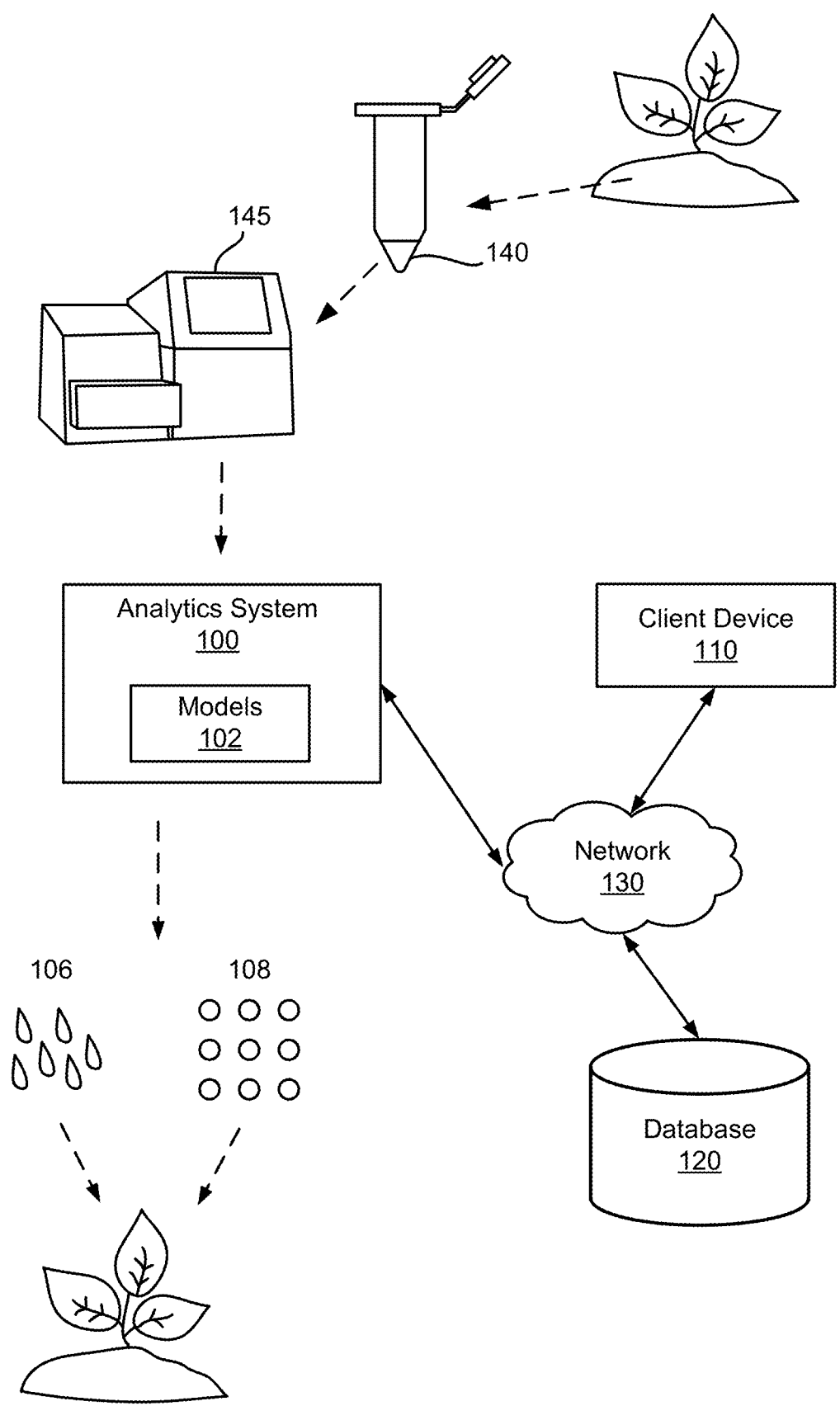
FIG. 1A illustrates an example system environment for an analytics system according to an embodiment.

FIG. 1A illustrates an example system environment for an analytics system 100 according to an embodiment. The system environment shown in FIG. 1A includes the analytics system 100, a client device 110, and a database 120, which are connected to each other via a network 130 (e.g., the Internet). In other embodiments, different or additional entities can be included in the system environment. For instance, the system environment may include a sequencer 145 to process one or more samples 140. For example, though only one client device 110 and database 120 is shown in FIG. 1A, the system environment may include additional client devices 110 and/or databases 120. The functions performed by the various entities of FIG. 1A may vary in different embodiments.

The analytics system 100 use metagenomics of a physical sample to train models and generate predictions associated with the physical sample. In the embodiment shown in FIG. 1A, a sample 140 of soil (e.g., in which a crop is grown or may be grown) is provided to the sequencer 145 for sequencing. The sequencer 145 performs sequencing (e.g., of DNA and/or RNA) and outputs sequence reads of the sample 140. The sequencer 145 may provide the output sequence reads to the analytics system 100. The sequencer 145 can be communicatively coupled to the analytics system 100 through a wireless, wired, or a combination of wireless and wired communication technologies. The analytics system 100 may use the sequence reads to identify presence or measure of one or more particular organisms in the soil from which the sample 140 was obtained. Additionally, the analytics system 100 may use these measures as features for a model 102 as further described below.

The analytics system 100 includes one or more models 102 that include features (also referred to herein as model features). In an embodiment, a model 102 of the analytics system 100 determine attributes that describe properties of soil samples, explanations of crop yields, and/or recommendations that may increase soil health or yield of crops that grow from the soil. The analytics system 100 may determine which features to include in a model 102 based on processing of soil samples or other types of physical or biological samples, e.g., measures of organisms from sequence reads. Additionally, the analytics system 100 may receive information associated with features from a database 120 or other sources. The information may indicate particular types of features to include in a model 102, or particular values of one or more features of a given sample, e.g., for use as training data. Based on predictions generated by models 102 regarding the target variable and/or any recommendations derived from those predictions, farmers or other users may be informed as to a variety of actions that determine inputs to use on fields, when to plant, where to plant, which crops to plant, and which varietals of those crops to plant. Other example inputs include an amount of water 106 or fertilizer 108 to apply to certain crops.

Though not shown in FIG. 1A, the analytics system 100 may include one or more processors for manipulating and processing data, a network connection for communicating with other devices, and a non-transitory computer-readable storage medium for storing data, program code, and/or program instructions associated with various applications. It is noted that a storage medium may include volatile memory (e.g., random access memory) and/or non-volatile storage memory such as hard disks, flash memory, and external memory storage devices. The one or more processors may execute instructions to perform steps of one or more processes, e.g., the methods described below with reference to FIGS. 1B and 7.

In some embodiments, the analytics system 100 uses one or more machine leaching algorithms such as supervised learning to train a model 102 or infer a function. The function may map input values for model features and corresponding trained coefficients for those model features to an output value for a "target variable" (or "output label") that describe an attribute of a subject (e.g., a plant or other organism). For example, the inputs may be the abundances counts of a number of (e.g., anywhere from a handful to hundreds of thousands) different microbial species, genes, or genetic fragments known as k-mers. Additionally, the analytics system 100 can consider for use as model features various concepts other than microbial abundances. For clarity, these are herein referred to as "metrics," and examples include rainfall, soil diversity, yield and so on. The value for the target variable estimated based on the model features may be classifications such as whether crop disease is present or likely to manifest, and/or estimates of various numerical values, such as yield predictions. Categorical labels (for training) and outputs (for model use) may be non-numerical, such as High/Medium/Low, or numerical values such as percentages or scaled or non-scaled values such as probabilities/likelihoods.

The analytics system 100 is capable of interpreting values of features of a trained model 102 to determine context for the target variable of the model 102. For example, the analytics system 100 predicts that a particular soil sample is likely to result in a high crop yield due to a certain set of one or more features (e.g., beneficial microbes) of the model 102. In some embodiments, the analytics system 100 trains a model 102 using a subset, i.e., a training set, of agricultural data. The trained model 102 is validated using held-out data, i.e., a test set, of the agricultural data to avoid or mitigate bias of the model 102. In some embodiments, the analytics system 100 retrains the model 102 using a set of top features (e.g., influential features on a target variable) determined during a previous training. Further, the model 102 is trained to determine predictions or metrics of other soil samples, e.g., received from farmers.

For purposes of explanation, this disclosure uses soil samples and the microbiome of the soil samples generally as example use cases, though the embodiments described herein may be adapted for systems and methods using other types of biological samples or physical samples. For instance, the biological sample may be at least in part a liquid or aqueous sample used for growing plants in a hydroponics system. As a different example, the biological sample may be a sample of a gut microbiome of a subject (e.g., a human or another type of organism), and the model 102 may be trained to generate predictions associated with physiology or other attributes of the subject.

The analytics system 100 determines microbial species, genes, genetic fragments, or additional metrics (which may be the output of unrelated models) that contribute to output of a trained model 102. In one embodiment, the analytics system 100 uses a Random Forest (RF) classifier. However, the analytics system 100 may also use other suitable types of classifiers or machine learning techniques, e.g., ElasticNet and Lasso type regressions, support vector machines, neural networks (e.g., single layer or multi-layer so-called "deep learning" models). The analytics system 100 may use one or more machine learning techniques for microbial candidate and consortia identification, soil-based phenotype prediction, dimensionality reduction in microbial and genetic analysis, or collapsing of taxonomic rank for feature selection, among other applications. In some embodiments, the analytics system 100 may use statistical processes such as linear regression instead of machine learning algorithms or other more complex deep learning algorithms.

A client device 110 comprises one or more computing devices capable of processing data as well as transmitting and receiving data over the network 130. For example, a client device 110 may be a desktop computer, a laptop computer, a mobile phone, a tablet computing device, an Internet of Things (IoT) device, or any other device having computing and data communication capabilities. The analytics system 100 may provide information to the client device 110 for presentation to a farmer or another user. The information may include recommendations or metrics determined by the analytics system 100 regarding a particular crop or group of crops.

II. Example Model Training

Figure 1B:
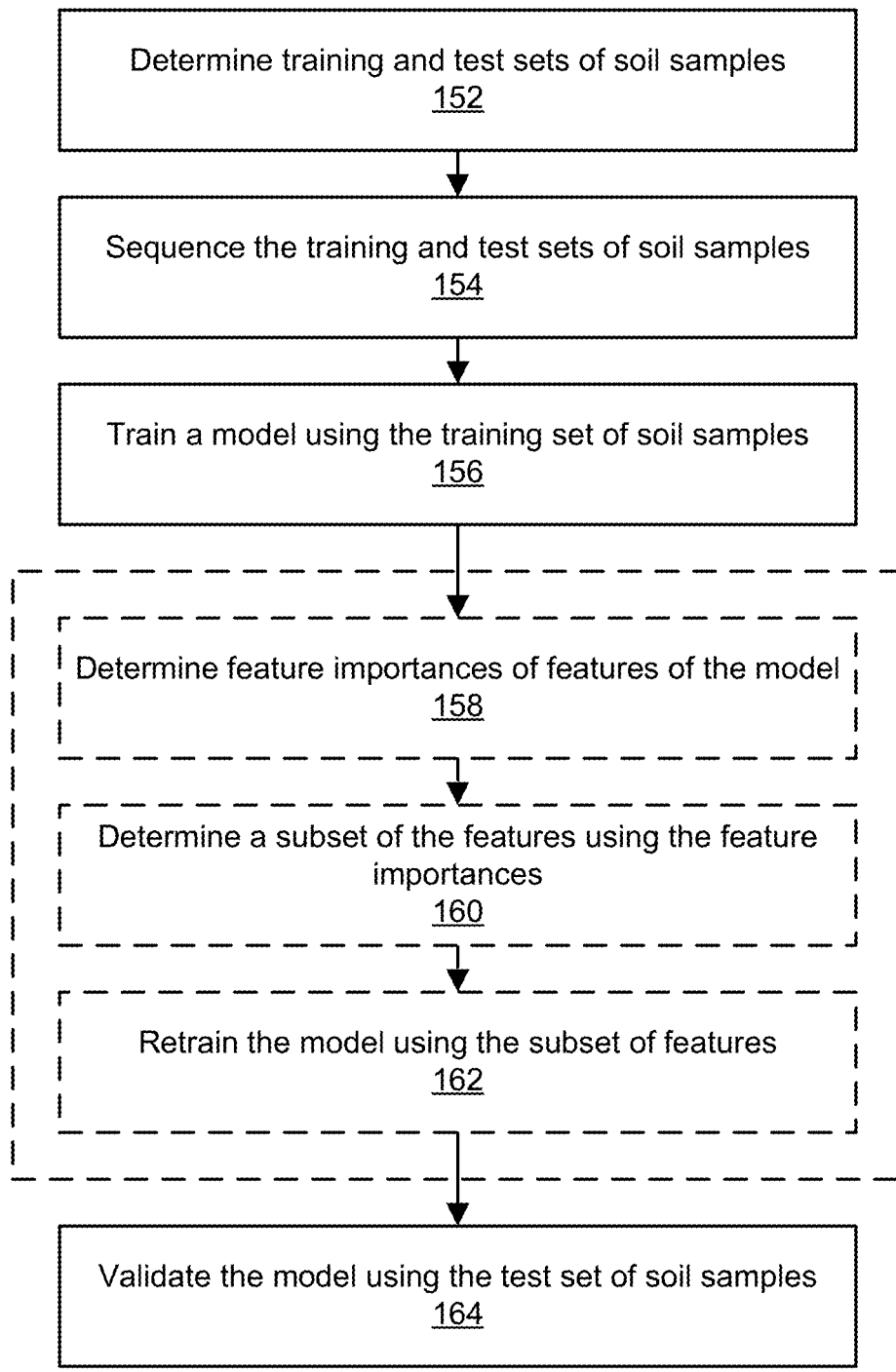
FIG. 1B illustrates an example process for training a model according to an embodiment.

FIG. 1B illustrates an example process 150 for training a model 102 according to an embodiment. Steps of the process 150 are described below with reference to FIGS. 2-6. In step 152, the analytics system 100 determines a training and test set of soil samples. The analytics system 100 may use a random selection process to determine the training and test sets from a dataset, and the portion selected for the test set may vary based on the dataset, for example, 20% of a dataset. The test set is separate from the training set for the purpose of attempting to prevent over-fitting of the model 102 to the training set. A trained model 102 may be fine-tuned for a specific dataset, though not necessarily generalize beyond the specific dataset.

II. A. Example Features

In step 154, the analytics system 100 sequences the training and test sets of soil samples. In an embodiment, the analytics system 100 uses shotgun metagenomic sequencing to generate a list of all organisms detected in a soil sample, as shown in the following example table. In some embodiments, the analytics system 100 uses next-generation sequencing (NGS). The analytics system 100 may identify the organisms by comparing sequence reads of nucleic acids (e.g., DNA or RNA) from the samples with reference sequence reads. Additionally, the analytics system 100 may determine a frequency of occurrence, or abundance percentage, for each organism. The analytics system 100 may determine and assign the frequencies at more than one level of the taxonomic tree (e.g., non-exclusively). For instance, *Fusarium oxysporum* f Sp. *Lactucae* is at the sub-species level of taxonomic rank, *Fusarium oxysporum* is at the species level, and *Fusarium* is at the genus level. The list of organisms (e.g., microbes) may also include multiple genera, e.g., *Bacillus* and *Fusarium*.

| Taxonomic unit name | Abundance percentage (out of 100 total) |
|---|---|
| *Fusarium oxysporum* f. sp. *lactucae* | 0.9 |
| *Fusarium oxysporum* | 1.5 |
| *Fusarium* | 47.2 |
| *Bacillus* | 12.1 |

The analytics system 100 may genetically sequence a set of soil samples to determine a "histogram" of microbes in the set (e.g., hundreds of thousands of microbes) with corresponding abundances, e.g., number of times each microbe was detected. In an embodiment, the analytics system 100 generates vectors of abundances for each microbe detected in a given sample. The vector may be represented by a data structure having length <1, number of microbes detected in the given sample>. In an example where few microbes are detected in a soil sample, the vectors may include many 0's.

In step 156, the analytics system 100 trains a model 102 using the training set of soil samples. A trained model 102 is configured to predict a value for a certain output label or target variable for a given biological (e.g., soil) sample. In addition to individual microbial abundances, various metrics can also be considered as input features to the model 102. Metrics may include, for example, outputs of additional models 102 that utilize other sequenced information from the biological sample, information associated with the sample that are non-biological in nature, or outputs from other models 102 not associated with the sample, among other types of metrics. Metrics may include a numerical or continuous value representing disease risk percentage, soil health, bacterial or fungal diversity, biomass, or fungal-to-bacterial ratio. A metric may also indicate a binary label (e.g., Boolean value), for example, whether the given soil sample is diseased or not diseased, presence of a particular organism, or abundance of a particular organism greater than a threshold value. In some embodiments, a model 102 may be trained using training data having labels corresponding to a binary label, for instance, one training data set corresponding to soil samples that developed a certain disease (e.g., "positive" label) and another training data set corresponding to different soil samples that did not develop the certain disease (e.g., "negative" label). In other embodiments, training data may have provided labels corresponding to three or more classifications.

The analytics system 100 may train the model 102 for regression (e.g., predicting a numerical or continuous value) or for classification (e.g., predicting a binary label). For purposes of explanation, this disclosure uses a Random Forest algorithm as one example for training models 102, though the embodiments described herein may be adapted for systems and methods using other suitable machine learning techniques or algorithms for training, for example, ElasticNet and Lasso type regressions, support vector machines, neural networks (e.g., single layer or multi-layer so-called "deep learning" models).

In an embodiment using a Random Forest algorithm, the analytics system 100 generates an ensemble of multiple Random Forest trees (e.g., around seven trees). To generate each tree, the analytics system 100 draws a subset of the data from the training set of soil samples. The analytics system 100 grows a Random Forest tree by recursively repeating steps for each terminal (or leaf) node of the tree until a minimum node size is reached. In an embodiment, the steps for processing a given node include (i) selecting a random subset of m variables from a predetermined set of p variables, (ii) determining a split point among the subset of m variables, and (iii) splitting the given node at the split point into two daughter nodes. The analytics system 100 may determine a regression prediction by averaging or otherwise combining outputs from the ensemble of trees. The analytics system 100 may determine a classification prediction (e.g., ensemble decision) according to a majority vote by the ensemble of trees. To improve or maximize performance of the training set for feature selection, the analytics system 100 may search and tune the parameter space of inputs to the Random Forest algorithm. Example parameters include maximum decision tree depth, leaf node splitting criteria (examples further described below), and number of subtrees in the forest that perform consensus voting to form the ensemble decision.

II. B. Example Dimensionality Reduction

In some embodiments, the analytics system 100 performs optional steps 158-162 (e.g., as indicated by the dotted lines shown in FIG. 1B) for dimensionality/feature reduction and retraining of the model 102. In step 158, the analytics system 100 determines feature importances for features of the model 102. A feature importance indicates the impact of a feature on the value of a given target variable associated with a model 102. For instance, predictions of the target variable generated by the model 102 may be influenced by some features to a greater degree than by other features.

II. B. I. Random Forest Tree

Figure 2:
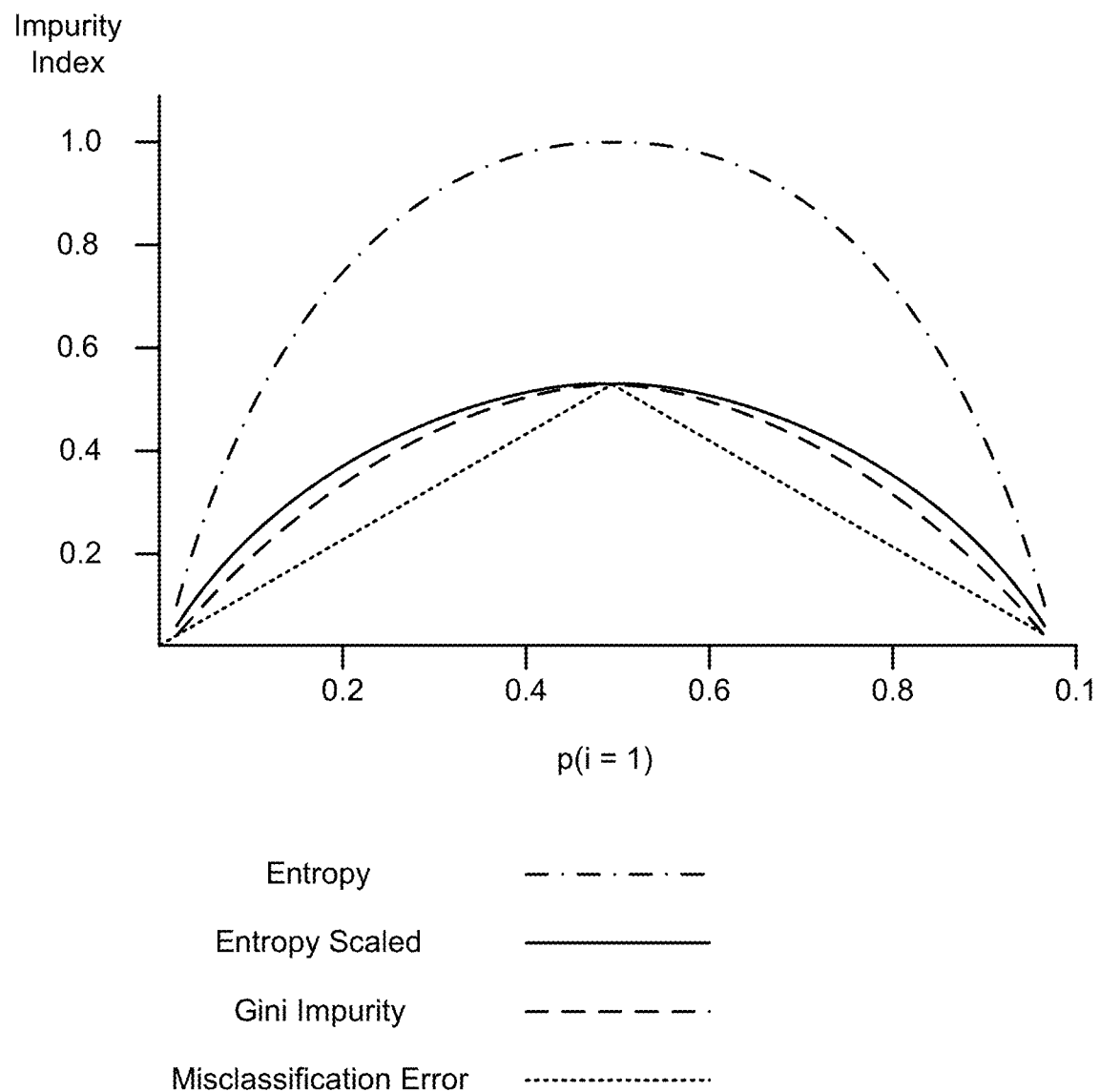
FIG. 2 illustrates an example diagram of entropy and Gini impurity functions according to an embodiment.

FIG. 2 illustrates an example diagram of entropy and Gini impurity functions according to an embodiment. In some embodiments, the analytics system 100 uses an entropy function or a Gini impurity function for a given feature to determine a split point for generating a Random Forest tree, e.g., to maximize information gain given by the corresponding split. An example entropy $I_H(t)$ and Gini Impurity $I_G(t)$ may be represented as a function of an input split t:

$$I_H(t) = -\sum_{i=1}^{c} p(i \mid t)\log_2 p(i \mid t)$$

$$I_G(t) = \sum_{i=1}^{c} p(i \mid t)(1 - p(i \mid t)) = 1 - \sum_{i=1}^{c} p(i \mid t)^2$$

The fraction p(i|t) is iterated over c different features, where p(i|t) represents the fraction of soil samples with feature i and split t. As shown in the diagram of FIG. 2, the entropy and Gini impurity functions may provide similar characteristics for maximization of feature importance. The analytics system 100 may further rank feature importance for determining the splits.

Figure 3:
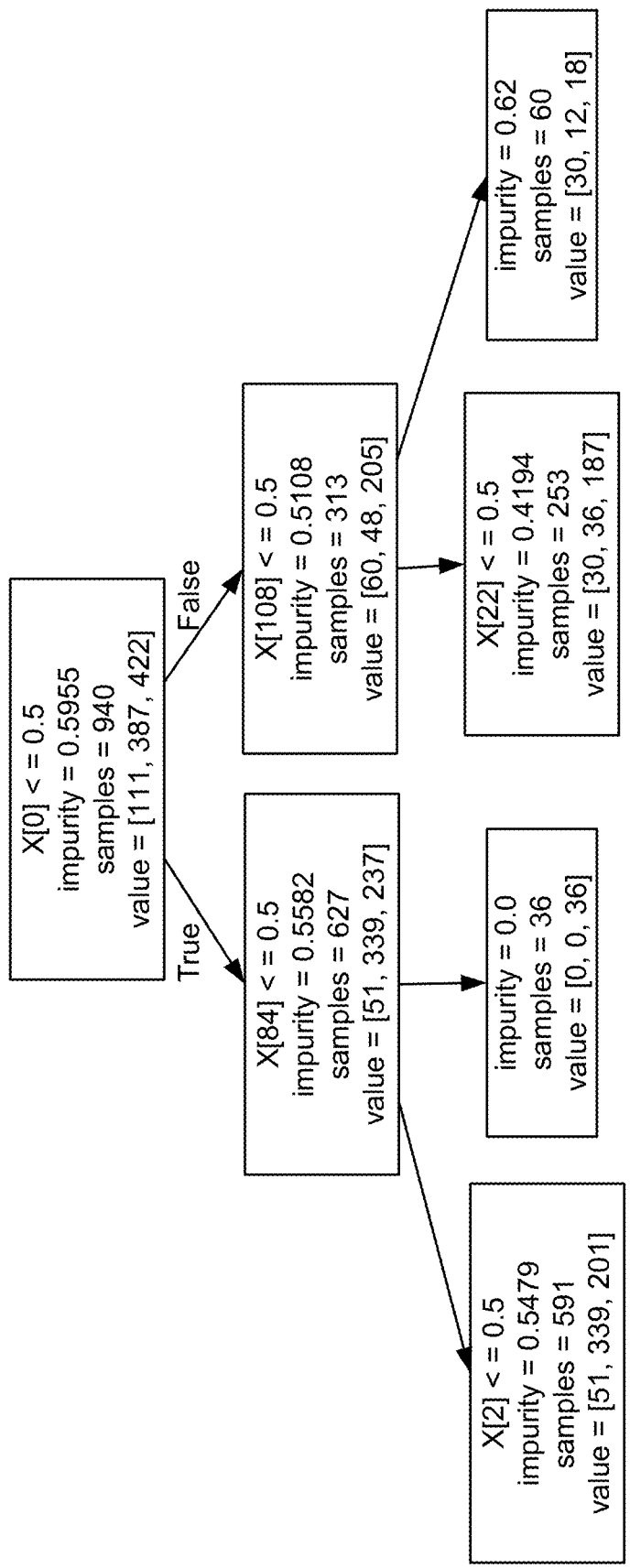
FIG. 3 illustrates an example diagram of a single tree of a Random Forest according to an embodiment.

FIG. 3 illustrates an example diagram of a single tree of a Random Forest according to an embodiment. Nodes of trees in the Random Forest are associated with a feature, e.g., X[0], X[1], X[2], etc., each of which represents an abundance of a certain microbe. Note that the example diagram illustrates only a portion of a complete tree, which may include additional nodes not shown in FIG. 3 for purposes of clarity. In addition, each node has a Gini impurity ("impurity"), a number of samples, and a set of classifications. Further, the set of classifications classify the soil sample as having low, medium, or high performance, e.g., "value=[111, 387, 442]" for the top node shown in FIG. 3.

The analytics system 100 may determine a magnitude of a change to a target variable resulting from a change of a given feature, e.g., splitting a node of the tree for a given microbe. In an embodiment, the analytics system 100 determines the feature importance of a tree by determining a change of a set of candidate changes that results in the maximum change to a value of the target variable, among the set (e.g., a local or global maxima). Thus, the analytics system 100 can use the feature importance to determine split points for maximizing information gain when generating trees. A high feature importance may indicate a strong positive or negative change to the value of the target variable.

II. B. II. Collapsing Taxonomic Rank

The analytics system 100 may determine abundance for organisms detected in a soil sample, as previously described. Granularity of the detected measure of abundances may include any number of taxonomic ranks or levels. An example hierarchy of taxonomic ranks includes (from general to specific): domain, kingdom, phylum, class, order, family, genus, and species. The analytics system 100 does not necessarily detect organisms in adjacent levels. For instance, the analytics system 100 may detect organisms at the family and species levels, without necessarily having to detect organisms at the genus level.

Figure 4:
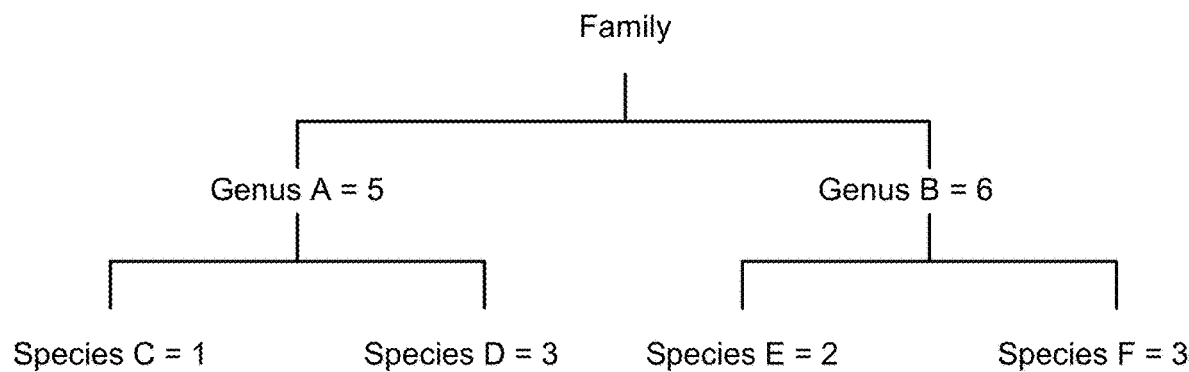
FIG. 4 illustrates collapsing of taxonomic rank for feature selection according to an embodiment.
Figure 4:
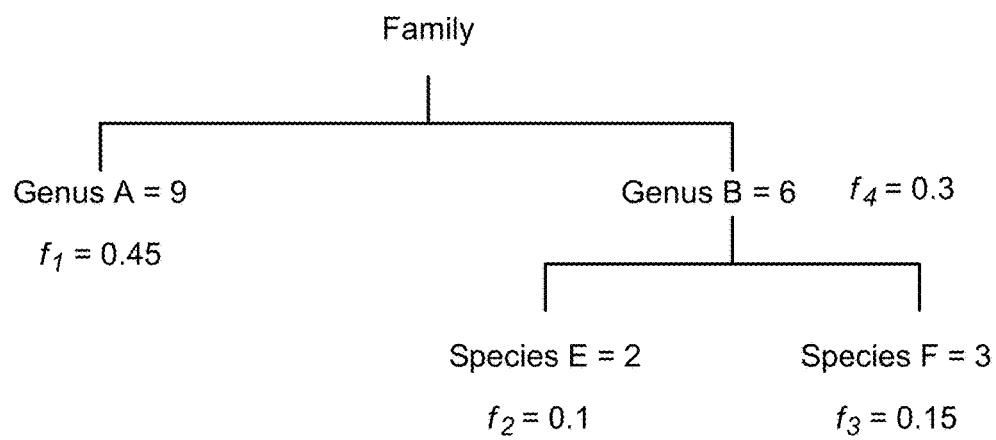

FIG. 4 illustrates collapsing of taxonomic rank for feature selection according to an embodiment. In some embodiments, the analytics system 100 performs collapsing of taxonomic rank ("coarse graining") to select a subset of features for training a model 102. The features may include collapsed measures (e.g., counts) of organisms. In the example diagram 400 of a taxonomic tree shown in FIG. 4, the analytics system 100 detects counts of organisms of genus A, genus B, species C, species D, species E, and species F, represented by nodes of the taxonomic tree. Genus A subsumes species C and species D, while genus B subsumes species E and species F. A family subsumes genus A and genus B. The example diagram 402 shows a collapsed version of the taxonomic tree of diagram 400. Particularly, the analytics system 100 collapses species C and species D to genus A. Thus, the analytics system 100 aggregates the measures of species C (i.e., 1) and species D (i.e., 3) with the measure of genus A (i.e., 5) to form a collapsed measure of nine at node A (1+3+5=9). In other use cases, the analytics system 100 may collapse nodes at different levels (e.g., order to class, or class to phylum), or may collapse multiple levels (e.g., species to genus, genus to family, and family to order). As shown in FIG. 4, the analytics system 100 may selectively collapse a given node or branch of the taxonomic tree and not necessarily another branch at the same level(s), e.g., the branch including genus B, species E, and species F.

The analytics system 100 may determine relative abundances of a collapsed taxonomic tree to be used as features. Following in the same example of FIG. 4, the collapsed taxonomic tree includes an aggregate measure (e.g., total count) of detected organisms totaling 20, which may be used to normalize the individual counts. The analytics system 100 determines the relative abundances (features) $f_1$=0.45, $f_2$=0.1, $f_3$=0.15, and $f_4$=0.3 for genus A, species E, species F, and genus B, respectively.

In some embodiments, the analytics system 100 accounts for interactions between features based on a product of two or more features. The product may be a polynomial product of values of the features. For instance, given $f_1$ and $f_2$, the analytics system 100 determines the polynomial product: $f_1^2+f_1f_2+f_2^2$. The analytics system 100 may use any number of the terms of the polynomial product as additional features for training. In the collapsed taxonomic tree of example diagram 402: $f_1^2$=0.45×0.45=0.2025, $f_1f_2$=0.45×0.1=0.045, and $f_2^2$=0.1×0.1=0.01. In some embodiments, the analytics system 100 accounts for interactions between different types of features. For example, interaction between relative abundance of a microbe and a numerical metric such as rainfall, temperature, or humidity may be used as a feature. In addition or as an alternative to collapsing taxonomic rank, the analytics system 100 may determine features by determining changes in detected organisms in a soil sample profiled at two or more different timestamps. In other embodiments, the analytics system 100 accounts for other types of interactions beyond a product or polynomial product. For instance, additional features may be derived using sums, differences, or other functions taking as input two or more features.

The analytics system 100 may determine feature importances of the features derived from a collapsed taxonomic tree using any of the processes described above in Section II. B. i. Random Forest Tree, or any other suitable process. Generally, the analytics system 100 determines greater feature importances for specific features, interaction between features, or temporal changes of features, that affect predictive accuracy of a model 102.

II. C. Example Feature Selection

In step 160, the analytics system 100 determines a subset of the features using the feature importances. The subset of the features may also be referred to as a "microbial consortium." In an embodiment, the analytics system 100 selects features (e.g., microbes) of the trained model 102 that influence predictions determined by the trained model 102. The analytics system 100 may select the subset of features based on an overall feature importance of the ensemble. In an embodiment using Random Forest Tree, the analytics system 100 uses the feature importances to determine an overall ranking of features (e.g., where a greater value of a feature importance is indicative of a greater influence on model 102 predictions) over an ensemble of B trees. The analytics system 100 may determine the overall ranking of features as the sum of the feature importance (feature importances) from each individual tree (e.g., of a microbe) in the ensemble divided by the number of trees in the ensemble, e.g., to determine an average feature importance:

$$\frac{1}{B} \cdot \sum_i^B \text{feature\_importances}_i$$

Figure 5:
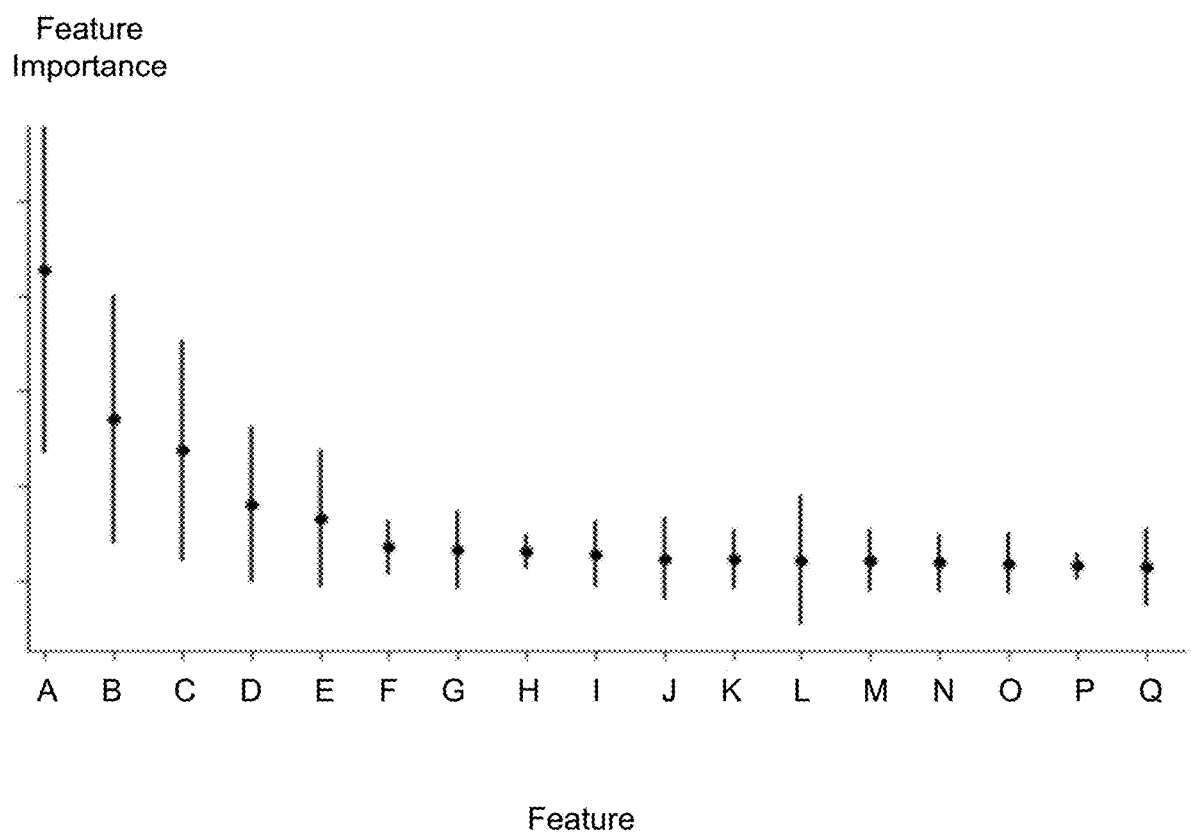
FIG. 5 illustrates an example diagram of feature importances of one or more soil samples according to an embodiment.

FIG. 5 illustrates an example diagram of feature importances for one or more soil samples according to an embodiment. The example diagram shows the feature importance of different features, e.g., Microbes A, B, C, . . . Q, for a target variable of plant weight. For instance, the analytics system 100 trains a model 102 to predict the weight of plants grown using soils that contain a composition of the different microbes corresponding to the features. In other embodiments, the model 102 may predict other types of plant phenotypes. Based on the example feature importance values shown in FIG. 5, the model 102 may determine that Microbe A may have a strong positive impact on the weight of a plant (e.g., improves resistance to diseases) and that Microbe B (e.g., a disease pathogen) may have a strong negative impact on weight. Though Microbe A and B are predicted to have beneficial and adverse effects, respectively, the magnitude of the feature importance for both may be high, in comparison to those of other microbes that may have a weaker or negligible impact on plant weight. In some embodiments, the microbes are labeled or categorized based on taxonomic rank.

In one use case, the analytics system 100 selects the subset by selecting a predetermined number (e.g., 5, 10, 25, 50, 100, etc.) or a percentage of features having the greatest feature importance. The predetermined number may be experimentally tuned. In another embodiment, the analytics system 100 iteratively selects an increasing (or decreasing) number or percentage of candidate features having the greatest feature importance, and retrains the model 102 using the candidate features until a threshold of model 102 performance is reached. The threshold may be a statistically determined value, e.g., based on when the feature importance tapers off, plateaus, or reaches a steady state value. The analytics system 100 may select a default number or percentage of features responsive to determining that the iterations exceed a time out duration or number of iterations. Selecting a predetermined number of features may help prevent overfitting a model 102 to a specific sample, while maintaining generality of the model 102 to generate accurate predictions across a range of samples, e.g., from fields in different geographic regions. In embodiments using polynomial products of features, the analytics system 100 may use dimensionality reduction to select features representing interactions that are more likely predictive of a target variable.

In step 162, the analytics system 100 retrains the model 102 using the subset of features. In embodiments using Random Forests, the analytics system 100 may ignore or remove (e.g., prune) the trees corresponding to the unselected features. By removing the features not included in the subset (e.g., features determined to have less impact on the target variable or output label relative to those in the subset), the analytics system 100 can perform dimensionality reduction in microbial and genetic analysis. Thus, results of the model 102 or explanation of predictions made by the model 102 may be more easily interpretable by a user of the analytics system 100. In some embodiments, the analytics system 100 does not necessarily need to retrain the model 102. For instance, the analytics system 100 may train the model 102 using information learned from previous steps of the process 100 or from other sources of training information.

Figure 6:
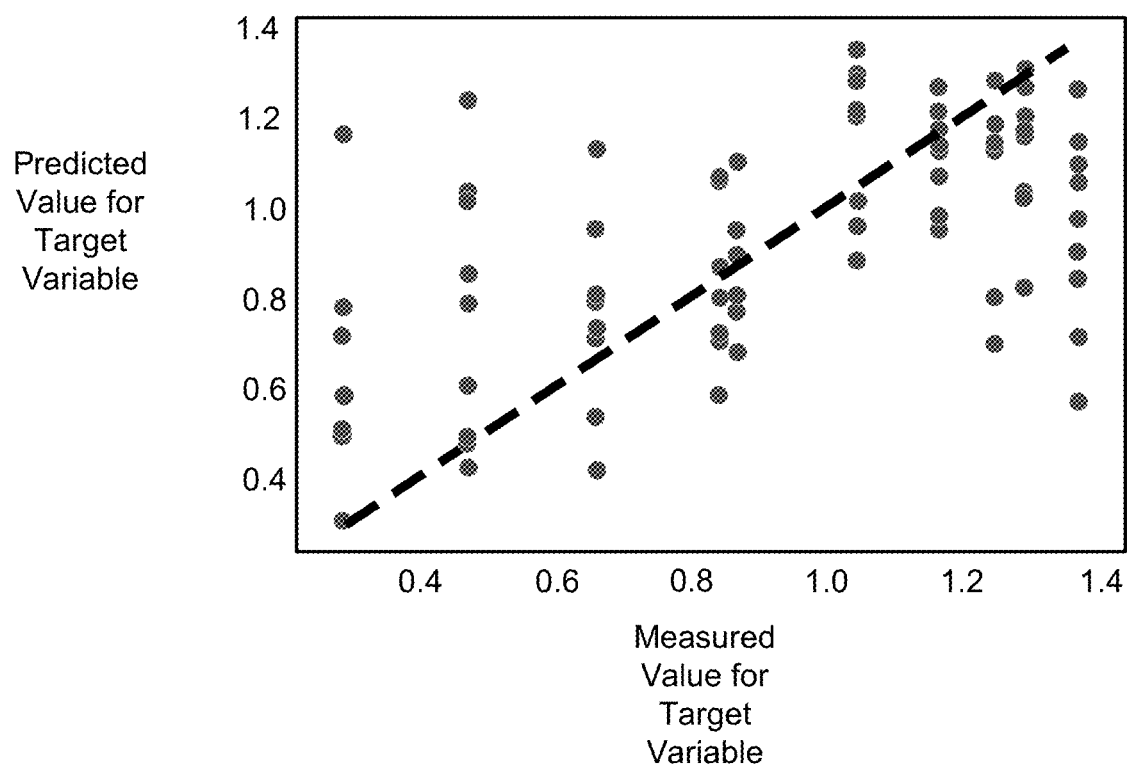
FIG. 6 illustrates an example diagram of predicted and measured values for a target variable of a soil sample according to an embodiment.

In step 164, the analytics system 100 validates the model 102 using the test set of soil samples. FIG. 6 illustrates an example diagram of predicted and measured values for a target variable of a soil sample according to an embodiment. In an embodiment, the analytics system 100 validates the retrained model 102 using predicted and measured values of the test set. The measured values shown on the x-axis in FIG. 6 are observed from the soil samples in the test set. The analytics system 100 inputs features of the test set into the retrained model 102 to generate predictions for the target variable shown on the y-axis in FIG. 6. The analytics system 100 may determine that the predicted values of the target variable (e.g., weight of plants grown from soil having a certain microbiome) are statistically significant. For instance, the analytics system 100 fits the predicted and measured values for the target variable using linear regression (e.g., as shown in the line in FIG. 6) and determines that the fit satisfies a criteria, e.g., a threshold correlation or R-squared value. Based on the validation, the analytics system 100 determines that the model 102 can make useful or statistically significant predictions using the selected microbial consortium and not necessarily having to use the remaining unselected microbes (or input features such as other metrics).

II. D. Example Single Feature Model

In an embodiment, the analytics system 100 trains a model 102 that generates predictions using a single feature. The single feature may represent a normalized measure of a given organism detected in a soil sample. As an example use case, a trained model 102 determines a likelihood of wilt disease developing in lettuce plants using relative abundance of detected organisms at the *Fusarium* genus level. The likelihood may be based on a function including one or more coefficients or weights applied to an input relative abundance. In another embodiment, the model 102 predicts wilt disease based on comparison with a threshold value. For instance, the model 102 predicts wilt disease will develop responsive to determining that the relative abundance is greater than (or less than or equal to) a threshold value. The threshold value may be determined by linear regression for binary classification.

II. E. Example Multiple Feature Model

In an embodiment, the analytics system 100 trains a model 102 that generates predictions using multiple features. As an example use case, a trained model 102 determines yield of corn plants using features including at least a measure of dry biomass and stem diameter. The measure of stem diameter may exhibit a bimodal distribution in a training data set. Accordingly, the model 102 may use a median stem diameter in training data to determine a threshold diameter value predictive of high or low growth. The model 102 may also use feature interactions between dry biomass, stem diameter, and other features.

III. Example Model Application

Figure 7:
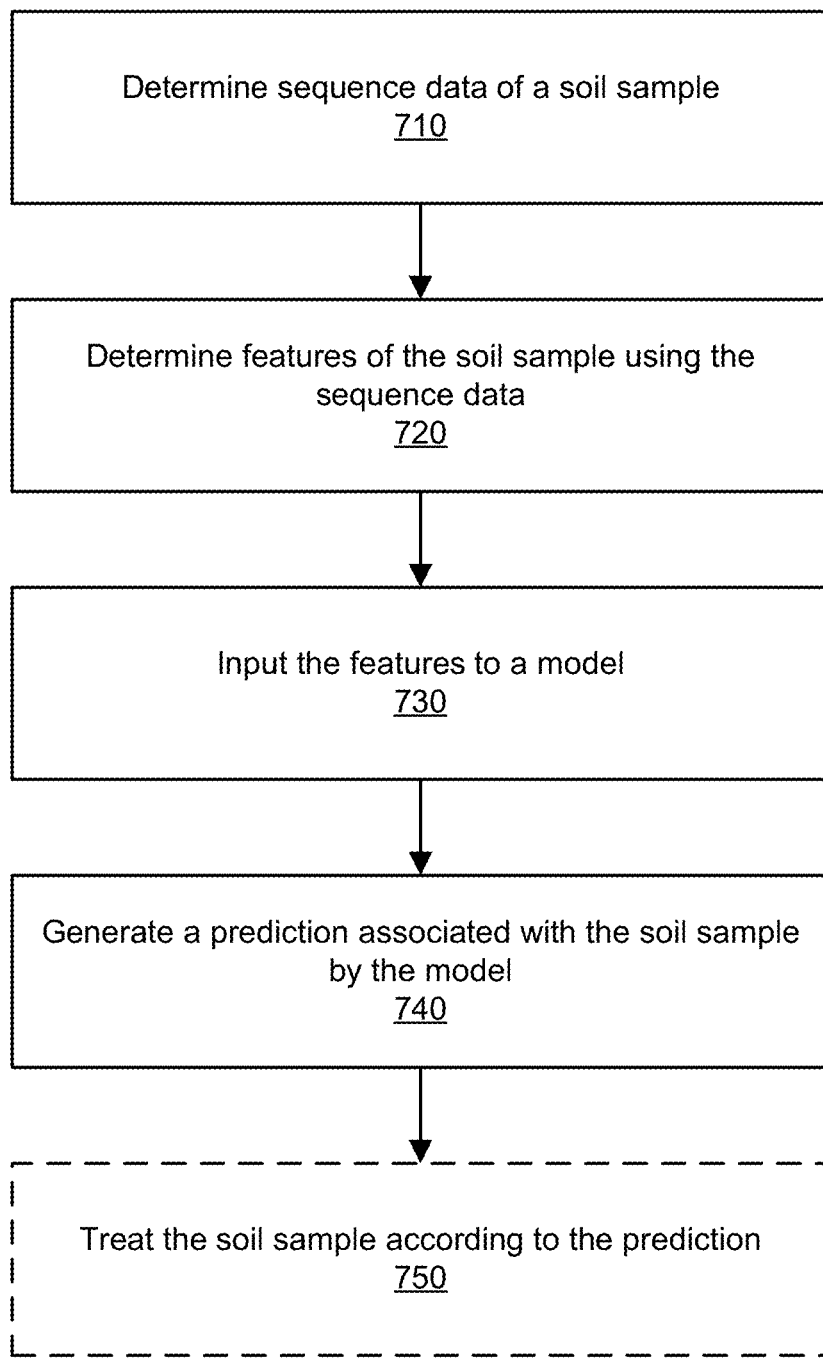
FIG. 7 illustrates an example process for evaluating and treating a soil sample according to an embodiment.

FIG. 7 illustrates an example process 700 for evaluating and treating a soil sample according to an embodiment. In step 710, the analytics system 100 determines sequence data of a soil sample. In step 720, the analytics system 100 determines features of the soil sample using the sequence data. The features may include microbial abundances and/or values of metrics. Microbial abundances represent measures of microbes detected in the soil sample according to sequence data. For instance, the analytics system 100 may compare raw DNA or RNA sequences in the sequence data with reference sequence data or signatures known to be associated with a particular organism, e.g., matched or collapsed to a certain taxonomic level. Thus, the analytics system 100 can identify the particular microbiome of the soil sample, which may differ based on geographic region, weather conditions, crops grown in the soil, or other parameters or attributes. The analytics system 100 may determine the microbial abundances according to a microbial consortium, e.g., determined using one or more steps of the process 150 shown in FIG. 1B. For instance, rather than determine abundance of all microbes present in the soil sample, the analytics system 100 may only determine the abundance of microbes included in the microbial consortium or corresponding to selected subset of features.

In some embodiments, the microbial abundances are determined using a collapsed taxonomic tree. Particularly, the analytics system 100 determines aggregate microbial abundance for a given node of a taxonomic tree by including microbial abundance from one or more other levels subsumed by the corresponding taxonomic level of the given node (e.g., as shown in FIG. 4). Further, the analytics system 100 may normalize measures of microbial abundances to use relative microbial abundances as input to a model. The analytics system 100 may determine multiple relative microbial abundances by collapsing taxonomic rank of any number of nodes of a taxonomic tree. The collapsed nodes may include any number of levels, and different types of levels may be collapsed between different nodes. In some embodiments, the analytics system 100 determines the microbial abundances using polynomial product of two or more features, which may represent relative microbial abundances determined using collapsed taxonomic rank. In some embodiments, the analytics system 100 performs center log transformation on features.

In step 730, the analytics system 100 inputs the features (microbial abundances and/or values of metrics) to a model 102 to generate a prediction. The model 102 may be trained, retrained, and/or validated using the process 150 shown in FIG. 1B, where the generated prediction corresponds to the target variable predicted by the model 102. In some embodiments, the model 102 is trained using measures of two or more microbes detected in soil samples (e.g., training data from a reference field). The inputs may include two or more relative microbial abundances (labeled at one or more specific taxonomic levels) that predict yield or another phenotype of a crop. In step 740, the model 102 generates the prediction associated with the soil sample. The prediction may indicate a target variable of the soil sample, for instance, a physical attribute (e.g., phenotype) of a plant grown in the soil sample. The predication may be a binary classification or an estimated numerical value of the target variable.

In an optional step 750, the soil sample is treated according to the prediction. The analytics system 100 may provide the prediction or other information associated with the prediction for presentation via a client device 110. For example, responsive to determining that a predicted plant weight of a crop is lower than average, a farmer may provide additional fertilizer or other types of substances to the crop. As another example, responsive to determining that the predicted plant weight of the crop is greater than average, a farmer may reduce an amount of subsequent fertilizer provided to the crop. The client device 110 may display on a user interface a recommend amount of fertilizer or water to provide to a crop based on a prediction. Additionally, the client device 110 may also display information describing a schedule for providing water or fertilizer. In one embodiment, the analytics system 100 may provide a command to a client device 110 or another type of device to automatically treat the soil sample with a treatment loaded onto the device. For instance, the device is a manned or autonomous tractor for applying fertilizer or water to crops.

FIG. 8 illustrates an example pathogens detected by one or more models 102 according to an embodiment. As shown by the table in FIG. 8, the analytics system 100 may train a model 102 to determine the effect of different pathogens on various types of crops.

IV. Additional Considerations

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method comprising:
receiving a soil sample from soil of a crop;
determining sequence data of the soil sample;
determining a first measure of a first microbe detected in the soil sample, wherein the first measure is associated with a first taxonomic level of a plurality of taxonomic levels including at least species, genus, and family;
determining a second measure of a second microbe detected in the soil sample, wherein the second measure is associated with a second taxonomic level of the plurality of taxonomic levels different than the first taxonomic level;
determining a plurality of features of the soil sample using the sequence data by aggregating the first measure of the first microbe detected in the soil sample and the second measure of the second microbe detected in the soil sample;

inputting the plurality of features to a model trained using measures of the first microbe and the second microbe detected in a plurality of soil samples;
generating, by the model using the plurality of features, a prediction of a physical attribute of the crop in the soil sample; and
providing, for display on a client device, a treatment to provide to the crop according to the prediction.

2. The method of claim 1, further comprising:
determining an aggregate measure of organisms in the soil sample;
determining a first relative abundance of the first microbe by normalizing the measure using the aggregate measure, wherein the first measure is the first relative abundance; and
determining a second relative abundance of the second microbe by normalizing the different measure using the aggregate measure, wherein the second measure is the second relative abundance.

3. The method of claim 2, further comprising:
determining a first product between a value of the first relative abundance and the value of the first relative abundance;
determining a second product between the value of the first relative abundance and a value of the second relative abundance; and
determining a third product between the value of the second relative abundance and the value of the second relative abundance.

4. The method of claim 2, wherein the plurality of features further includes a third relative abundance of a third microbe associated with a third taxonomic level of the plurality of taxonomic levels different than the first taxonomic level and the second taxonomic level.

5. The method of claim 1, wherein the plurality of taxonomic levels further includes at least phylum, class, and order.

6. The method of claim 1, further comprising:
treating the soil sample according to the prediction.

7. A system comprising a computer processor and a memory, the memory storing computer program instructions that when executed by the computer processor cause the processor to perform steps comprising:
determining sequence data of a soil sample from soil of a crop;
determining a first measure of a first microbe detected in the soil sample, wherein the first measure is associated with a first taxonomic level of a plurality of taxonomic levels including at least species, genus, and family;
determining a second measure of a second microbe detected in the soil sample, wherein the second measure is associated with a second taxonomic level of the plurality of taxonomic levels different than the first taxonomic level;
determining a plurality of features of the soil sample using the sequence data by aggregating the first measure of the first microbe detected in the soil sample and the second measure of the second microbe detected in the soil sample;
inputting the plurality of features to a model trained using measures of the first microbe and the second microbe detected in a plurality of soil samples;
generating, by the model using the plurality of features, a prediction of a physical attribute of the crop in the soil sample; and
providing, for display on a client device, a treatment to provide to the crop according to the prediction.

8. The system of claim 7, further comprising:
determining an aggregate measure of organisms in the soil sample;
determining a first relative abundance of the first microbe by normalizing the measure using the aggregate measure, wherein the first measure is the first relative abundance; and
determining a second relative abundance of the second microbe by normalizing the different measure using the aggregate measure, wherein the second measure is the second relative abundance.

9. The system of claim 8, further comprising:
determining a first product between a value of the first relative abundance and the value of the first relative abundance;
determining a second product between the value of the first relative abundance and a value of the second relative abundance; and
determining a third product between the value of the second relative abundance and the value of the second relative abundance.

10. The system of claim 8, wherein the plurality of features further includes a third relative abundance of a third microbe associated with a third taxonomic level of the plurality of taxonomic levels different than the first taxonomic level and the second taxonomic level.

11. The system of claim 7, wherein the plurality of taxonomic levels further includes at least phylum, class, and order.

12. A non-transitory computer-readable storage medium storing instructions for controlling a computer system to:
determine sequence data of a soil sample from soil of a crop;
determine a first measure of a first microbe detected in the soil sample, wherein the first measure is associated with a first taxonomic level of a plurality of taxonomic levels including at least species, genus, and family;
determine a second measure of a second microbe detected in the soil sample, wherein the second measure is associated with a second taxonomic level of the plurality of taxonomic levels different than the first taxonomic level;
determine a plurality of features of the soil sample using the sequence data by aggregating the first measure of the first microbe detected in the soil sample and the second measure of the second microbe detected in the soil sample;
input the plurality of features to a model trained using measures of the first microbe and the second microbe detected in a plurality of soil samples;
generate, by the model using the plurality of features, a prediction of a physical attribute of the crop in the soil sample; and
provide, for display on a client device, a treatment to provide to the crop according to the prediction.

13. The non-transitory computer-readable storage medium of claim 12, storing further instructions for controlling the computer system to:
determine an aggregate measure of organisms in the soil sample;
determine a first relative abundance of the first microbe by normalizing the measure using the aggregate measure, wherein the first measure is the first relative abundance; and determine a second relative abundance of the second microbe by normalizing the different measure using the aggregate measure, wherein the second measure is the second relative abundance.

14. The non-transitory computer-readable storage medium of claim 12, storing further instructions for controlling the computer system to:
determine a first product between a value of the first relative abundance and the value of the first relative abundance;
determine a second product between the value of the first relative abundance and a value of the second relative abundance; and
determine a third product between the value of the second relative abundance and the value of the second relative abundance.

\* \* \* \* \*